| (12) | United States Patent | (10) Patent No.: | US 8,798,752 B2 |
|---|---|---|---|
| | Eder et al. | (45) Date of Patent: | Aug. 5, 2014 |

(54) REMOVABLE IMPLANTABLE BATTERY POSITIONED INSIDE IMPLANT COIL

(75) Inventors: Helmut Eder, Bemboka (AU); Dirk Fiedler, Elanora Heights (AU)

(73) Assignee: Cochlear Limited, Macquarie University, NSW (AU)

( * ) Notice: Subject to any disclaimer, the term of this patent is extended or adjusted under 35 U.S.C. 154(b) by 449 days.

(21) Appl. No.: 13/002,480

(22) PCT Filed: Jul. 2, 2009

(86) PCT No.: PCT/AU2009/000853
§ 371 (c)(1),
(2), (4) Date: May 11, 2011

(87) PCT Pub. No.: WO2010/000027
PCT Pub. Date: Jan. 7, 2010

(65) Prior Publication Data
US 2011/0208267 A1    Aug. 25, 2011

(30) Foreign Application Priority Data
Jul. 3, 2008   (AU) .............................. 2008903432

(51) Int. Cl.
*A61N 1/375*   (2006.01)
*A61N 1/378*   (2006.01)

(52) U.S. Cl.
CPC .............. *A61N 1/375* (2013.01); *A61N 1/3758* (2013.01); *A61N 1/3787* (2013.01)
USPC ............................................................ 607/37

(58) Field of Classification Search
CPC ...... A61N 1/375; A61N 1/3758; A61N 37/87
USPC ....................................................... 607/36–37
See application file for complete search history.

(56) References Cited

U.S. PATENT DOCUMENTS

| 6,240,318 B1 | 5/2001 | Phillips | |
|---|---|---|---|
| 2004/0260362 A1 | 12/2004 | Darley | |
| 2006/0183965 A1* | 8/2006 | Kasic et al. ..................... | 600/25 |
| 2007/0067000 A1* | 3/2007 | Strother et al. ................. | 607/36 |
| 2007/0156011 A1 | 7/2007 | Westerkull | |

OTHER PUBLICATIONS

International Search Report for PCT/AU2009/000853, mailed Sep. 25, 2009, 5 pages.

* cited by examiner

*Primary Examiner* — Amanda Patton
(74) *Attorney, Agent, or Firm* — K&L Gates, LLP

(57) ABSTRACT

An implantable component of a prosthesis comprising of at least one powered component; at least one antenna coil contained within an electrically insulating surround; and an electrical storage element for powering at least one powered component, the electrical storage element being positionable within a support area of the surround, the support area being at least partially within the area defined by the at least one antenna coil.

19 Claims, 2 Drawing Sheets

REMOVABLE IMPLANTABLE BATTERY POSITIONED INSIDE IMPLANT COIL

CROSS-REFERENCE TO RELATED APPLICATION

The present application is a National Stage application of International Patent Application No. PCT/AU2009/000853, filed Jul. 2, 2009, and claims priority from Australian Patent Application No. 2008903432, filed Jul. 3, 2008. The content of these applications are hereby incorporated by reference herein.

BACKGROUND

1. Field of the Invention

The present invention relates to generally to medical devices, and more particularly to an implantable component of a medical device.

2. Related Art

Auditory prostheses, such as cochlear implants, typically comprise an external component, such as a sound processor unit, and an implantable component, such as a receiver/stimulator unit. The external component typically comprises a casing, a microphone, a processing circuit that converts detected sounds into coded signals, and a power source. The implantable component receives the coded signals and power from the external component and sends a stimulation signal to an electrode assembly that applies electrical stimulation to the auditory system of the implantee producing a hearing sensation corresponding to the original detected sound.

Communication between the external component and the implantable component can be provided by a radio frequency (RF) magnetic induction link comprising an inductively coupled external antenna coil and an internal implanted antenna coil. This RF link provides transcutaneous transmission of the coded signals to, and also typically from, the implantable component and can also serve to provide power to the implantable component. Implantable components having an onboard rechargeable battery have also been proposed. Such prostheses can utilise more than one type of external component or work together with other external or implantable components.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In one aspect of the present invention, there is provided an implantable component of a prosthesis comprising: at least one component that uses power; an electrically insulating surround; at least one antenna coil contained within the electrically insulating surround, the at least one antenna coil defining an area; and an electrical storage element configured to provide power to said at least one component, the electrical storage element being positionable within a support area of the surround, said support area being at least partially within the area defined by the at least one antenna coil.

In another aspect of the present invention, there is provided an implantable component of a prosthesis comprising: at least one component that uses power; at least one antenna coil contained within an electrically insulating surround; and a power source for powering the at least one component, the power source comprising: an electrical storage element; a control device; and a power source antenna coil; wherein said at least one antenna coil and said power source antenna coil are respectively positioned to form a magnetic induction link for transmitting at least power from the electrical storage element to the at least one component.

BRIEF DESCRIPTION OF THE DRAWINGS

By way of example only, embodiments of the invention are now described with reference to the accompanying drawings.

DETAILED DESCRIPTION

Figure 1:
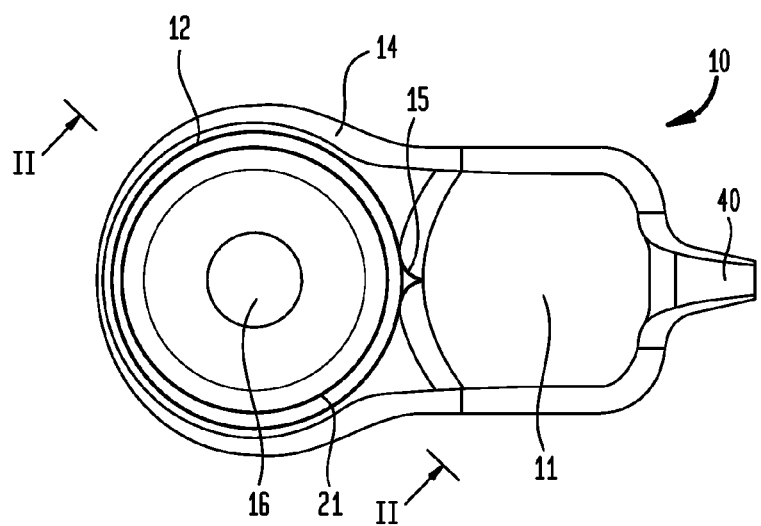
FIG. 1 is a plan view of an implantable component in accordance with the present invention.

The embodiment of the invention depicted in the drawings is shown as part of a cochlear implant system. It is to be understood that the present invention has application to other implantable prostheses including but not limited to auditory prostheses.

One embodiment of an implantable component of a cochlear implant system according to an embodiment of the present invention is generally depicted as 10 in FIG. 1. The implantable component 10 of the prosthesis has a hermetically sealed titanium housing 11 that contains components (e.g., circuitry) for operation of the component 10 that require power to operate.

The component 10 also has an antenna coil 12 comprising two platinum or gold windings 13 that are contained within an electrically insulating surround 14. Electrical connection between the componentry of the housing 11 and the antenna coil 12 is made by way of leads 15 that extend to feedthroughs formed in the wall of the housing 11.

Positioned and supported within the area defined by the windings 13 is an on-board power source 16 that can be used to provide power for the components within the housing 11.

Figure 2:
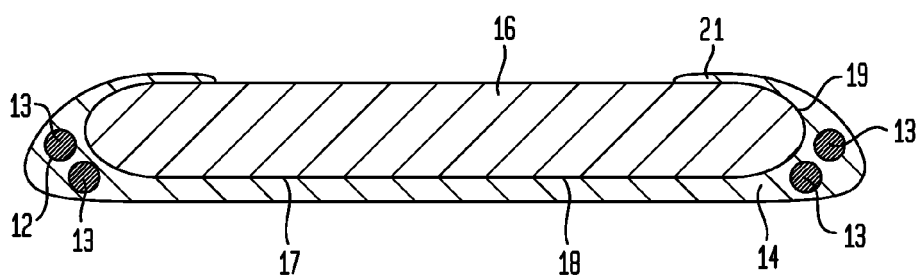
FIG. 2 is a cross-sectional view through lines II-II of FIG. 1.

As depicted in FIG. 2, the power source 16 can be removably positioned in a support area within the electrically insulating surround 14. In the depicted embodiment, the surround 14 comprises an elastomeric or polymeric member, for example, a silicone rubber. The support area as depicted comprises a pocket 17 that receives the power source 16. The depicted pocket 17 is substantially circular and has a base 18, an outer wall 19, and a top lip 21 that partially overlies the power source 16 when it is positioned within the pocket 17. The top lip 21 serves to hold the power source 16 in place but can be readily manipulated to allow the power source 16 to be removed from the pocket 17.

The windings 13 of the at least one antenna coil 12 of the implantable component 10 are positioned within the surround 14 at a location outwardly from the pocket 17. As depicted, at least one winding 13 of the antenna coil 12 can be positioned within the base 18 and/or outer wall 19 of the surround.

Figure 3:
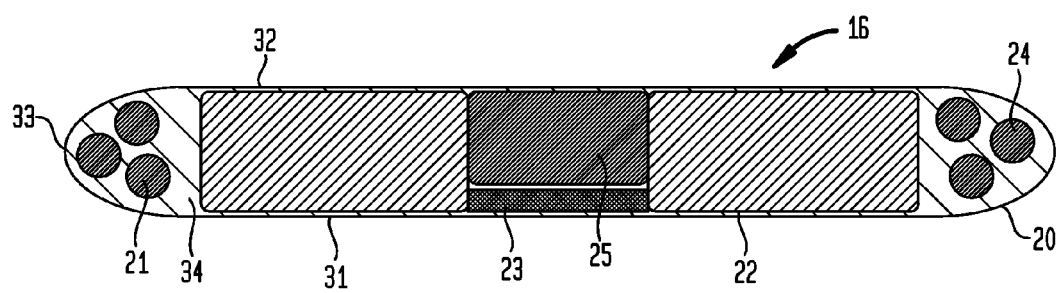
FIG. 3 is a cross-sectional view of one embodiment of a power source in accordance with the present invention.
Figure 4:
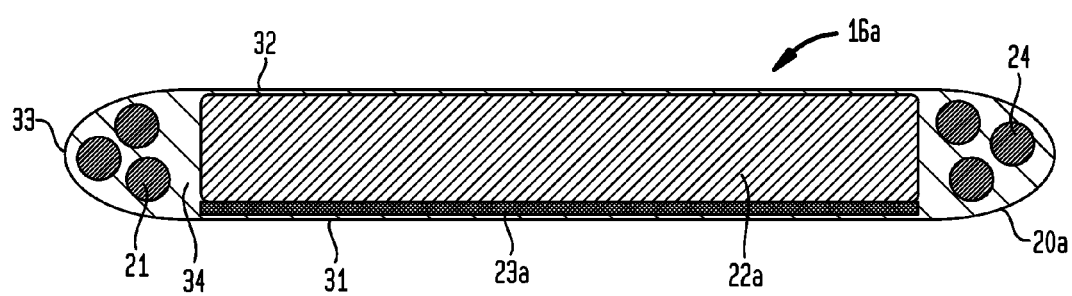
FIG. 4 is a cross-sectional view of another embodiment of a power source in accordance with the present invention.

Examples of power sources are depicted in FIGS. 3 and 4.

As depicted in FIG. 3, the power source 16 can comprise an enclosure 20 containing an electrical storage element (here a battery 22), a control device 23, and a power source antenna coil 24. The windings 13 of the antenna coil 12 and the power source antenna coil 24 can be respectively positioned to form a magnetic induction link for transmitting at least power from the battery 22 to the componentry within the housing 11.

The control device 23 can have a number of roles. For example, the control device can monitor and/or control the operation and use of the battery 22 and the transfer of power from the battery 22 to the componentry within the housing 11. In addition, the control device 23 can also be suitable for monitoring and/or controlling the charging of the battery 22 when an external antenna coil is brought into alignment with the power source antenna coil 24 to provide a radio frequency transcutaneous induction link for delivery of power to the battery 22. The control device 23 can have a rectifier, for example an arrangement of at least one diode, for rectifying the current induced in the power source antenna coil 24.

The enclosure 20 of the power source 16 can also contain a magnet 25. In the embodiment depicted in FIG. 3, the magnet 25 can be positioned at the centre of the power source 16. The magnet 25 can be cylindrical in shape but other shapes can be envisaged.

In another embodiment depicted in FIG. 4, the enclosure 20a of the power source 16a is itself formed partially or wholly from magnetic material. This allows removal of a separate magnet from the power source 16a and so allows placement of a larger rechargeable battery 22a within the enclosure 20a. It also potentially provides further space for the control device 23a.

The presence of the magnet 25 or the magnetic enclosure 20a allows the antenna coil 12 and/or the power source antenna coil 24 to be aligned appropriately with an external antenna coil that is also held on, for example, the outside of the head of the implantee by the magnetic force.

The battery 22, 22a can comprise at least one rechargeable battery. The battery can be nickel-based, for example a nickel cadmium (NiCd) battery, a nickel-metal hydride (NiMH) battery, or a nickel zinc (NiZn) battery. The battery can be silver-based, for example a silver oxide-zinc (Ag2OZn) battery. The battery can be lithium-based, for example a lithium-ion (Li-ion) battery or a lithium-metal battery. Exemplary Li-ion battery materials include lithium cobaltate, lithium manganate, lithium vanadate, lithium iron phosphate, lithium titanate, or mixed oxide or phosphate materials.

Any of the above exemplary battery technologies can have a liquid, partially or essentially fully immobilised, or solid-state electrolyte. The whole battery may be comprised entirely of solid-state materials without any added liquids in its final state.

An illustrative example is an all-solid state lithium-metal/ LiPON (lithium phosphor-oxynitride)/lithium cobaltate battery core, with appropriate current collectors.

In one embodiment, the battery 22, 22a can have mass or sintered electrodes. In this and other embodiments, the battery 22, 22a can have strongly alkaline electrolyte solutions that may be immobilised or gelified in order to reduce or prevent leakage.

The enclosures 20, 20a of the power sources 16, 16a can be hermetically sealed. In one embodiment, the enclosures 20, 20a can be substantially or wholly cylindrical having a bottom wall 31, a top wall 32 and a concave outer wall 33. The control device 23, 23a can also have an outer housing that is capable of preventing ingress of moisture into the control device 23, 23a. The enclosure 20, 20a and/or housing of the control device 23, 23a can be comprised wholly or in part of a relatively hard biocompatible overmould. While not necessary, the overmould can be partially, substantially or wholly filled with a relatively electrically insulating material. The overmould can be partially or wholly covered with an encapsulant material. The encapsulant can be a suitable elastomeric or polymeric or thermoplastic material. For example, the encapsulant can be parylene or liquid crystal polymer.

As depicted in FIGS. 3 and 4, the enclosure 20, 20a of the power source 16, 16a can also house the power source antenna coil 24. The windings of the power source antenna coil 24 can be formed of platinum or gold and are contained within the enclosure 20, 20a. The power source antenna coil 24 can, as depicted, comprise three windings. The antenna coil 24 can be supported by the relatively electrically insulating material within the overmould, when the material is present.

As depicted in FIG. 1, the elastomeric surround 14 can extend not just around the antenna coil 12 but also around the housing 11.

The housing 11 of the implantable component 10 contains a receiver/stimulator unit for a cochlear implant. While the component 10 can operate in conjunction with one or more external components, the depicted component because of its on-board power source 16, 16a can also or instead operate in a stand-alone fashion. While not depicted, the component 10 could comprise a totally implantable cochlear implant and have as well an on-board microphone, a speech processor, the stimulator/receiver unit, and at least an intracochlear electrode assembly. In such an embodiment, the implantable component 10 can at least operate for a portion of time without the need for an external component to be mounted on the implantee as the on-board power source 16, 16a provides the necessary power for the device while the power source has sufficient charge.

As described above, it will be appreciated that the component 10 could operate in conjunction with one or more external components. Such an external component could be used to recharge the power source 16, 16a. Still further, it could be used in conjunction with the implantable component 10 to provide a hearing sensation to an implantee. It will be appreciated that a different or the same external component can be used to recharge the power source 16, 16a and work in conjunction with the implantable component 10 to provide the hearing sensation. In one embodiment, the external component can have a microphone for detecting sound, a speech processor that converts the detected sounds, particularly speech, into a coded signal, a power source such as a battery, and an external transmitter antenna coil. The receiver/stimulator unit in the housing 11 of the implantable component 10 can receive the coded signal transmitted from the speech processor, process the coded signal and output a stimulation signal. The stimulation signal can be output to an electrode assembly, such as an intracochlear electrode assembly. In the depicted embodiment, the electrode assembly is not depicted for reasons of clarity but will extend from the housing 11 through feedthrough 40. The electrode assembly then delivers electrical stimulation to the auditory nerve of the implantee producing a hearing sensation corresponding to the original detected sound. The implantable component 10 can use the input from the external component when it is present but rely on the on-board componentry when the external component is not being used.

The intracochlear electrode assembly can comprise a carrier member having a leading end that is insertable into a cochlea of the implantee and a trailing end. The carrier can be formed of an elastomeric material, for example a silicone rubber material. The carrier member can have a plurality of electrodes mounted thereon. In one embodiment, the electrodes are mounted in a longitudinal array. Each of the electrodes can have at least one wire, for example two, extending from each electrode back towards the trailing end of the carrier member and then through a cable that extends back to the housing 11 at feedthrough 40 of the implantable component 10.

The carrier can have 22 electrodes. In another embodiment, the carrier can have 30 electrodes. Other numbers of electrodes can be utilised, including less than 20 electrodes, between 20 and 30 electrodes, and more 30 electrodes. The electrodes can be formed from a biocompatible electrically conducting material, such as platinum.

In another embodiment, the implantable component 10 can have a second electrode assembly extending from the housing (not depicted). The second electrode assembly may have one or more electrodes. This electrode assembly can be mounted within or external the cochlea of the implantee.

In one embodiment, the housing of the implantable component 10 can be positioned subcutaneously and, if required, within a recess in the temporal bone of the implantee.

Embodiments of the present invention allow for a relatively more straightforward replacement of an on-board power source 16, 16a of the implantable component 10 if and when required. This can be achieved, for example, by surgically accessing the implantable component 10, removing the power source 16, 16a from the pocket 17 of the surround 14 and replacing it with a new power source. Use of a power source antenna coil 24 to deliver power through a magnetic induction link to the componentry in the housing 11 of the implantable component 10 also removes the need for a connector or feedthrough to exist between the power source 16, 16a and the housing 11. This also allows relatively more ready replacement of the power source 16, 16a as there is no need to disconnect a lead extending from the power source 16, 16a to the housing 11. The lack of a connector or feedthrough also improves the hermeticity of the housing 11.

It will be appreciated by persons skilled in the art that numerous variations and/or modifications may be made to the invention as shown in the specific embodiments without departing from the scope of the invention as broadly described.

The present embodiments are, therefore, to be considered in all respects as illustrative and not restrictive.

The invention claimed is:

1. An implantable component of a prosthesis comprising:
   at least one component that uses power;
   an electrically insulating surround;
   at least one antenna coil contained within the electrically insulating surround, the at least one antenna coil defining an area; and
   a power source including a power source antenna coil and an electrical storage element configured to provide power to said at least one component, the electrical storage element being positionable within a support area of the surround, said support area being at least partially within the area defined by the at least one antenna coil.

2. The implantable component of claim 1 wherein the power source further comprises a control device.

3. The implantable component of claim 2 wherein the power source further comprises:
   a hermetically sealed enclosure in which the electrical storage element; the control device; the power source antenna coil; and a magnet are located.

4. The implantable component of claim 3 wherein the enclosure is at least partially formed from magnetic material.

5. The implantable component of claim 1, wherein the electrical storage element is removably positioned in the support area of the electrically insulating surround.

6. The implantable component of claim 5 wherein the surround comprises an elastomeric or polymeric member.

7. The implantable component of claim 1 wherein the implantable component is a component of an auditory prosthesis.

8. The implantable component of claim 7 wherein the auditory prosthesis is a cochlear implant.

9. The implantable component of claim 1, wherein the power source is removably positioned in the support area of the electrically insulating surround.

10. The implantable component of claim 9 wherein the support area comprises a pocket that is substantially circular and has a base, an outer wall and a top lip that partially overlies the power source when it is positioned within the pocket.

11. The implantable component of claim 1 wherein the implantable component is a component of an auditory prosthesis.

12. The implantable component of claim 11 wherein the auditory prosthesis is a cochlear implant.

13. The implantable component of claim 1, wherein said at least one antenna coil and said power source antenna coil are respectively positioned to form a magnetic induction link for transmitting at least power from the electrical storage element to the at least one component.

14. An implantable component of a prosthesis comprising:
   at least one component that uses power;
   at least one antenna coil contained within an electrically insulating surround; and
   a power source for powering the at least one component, the power source comprising:
      an electrical storage element;
      a control device; and
      a power source antenna coil;
   wherein said power source and said power source antenna coil are respectively positioned at least partially within an area defined by the at least one antenna coil so as to form a magnetic induction link for transmitting at least power from the electrical storage element to the at least one component.

15. The implantable component of claim 14, wherein the support area comprises a pocket that is substantially circular and has a base, an outer wall and a top lip that partially overlies the power source when it is positioned within the pocket.

16. The implantable component of claim 14, wherein the power source further comprises:
   a hermetically sealed enclosure in which the electrical storage element, the control device, the power source antenna coil, and a magnet are located.

17. The implantable component of claim 16, wherein the enclosure is at least partially formed from magnetic material.

18. The implantable component of claim 14 wherein the implantable component is a component of an auditory prosthesis.

19. The implantable component of claim 18 wherein the auditory prosthesis is a cochlear implant.

* * * * *